(12) United States Patent
Cox

(10) Patent No.: US 6,540,711 B2
(45) Date of Patent: Apr. 1, 2003

(54) KNEE BRACE

(76) Inventor: Michael F. Cox, 10138 Lexington Estates Blvd., Boca Raton, FL (US) 33428

(*) Notice: Subject to any disclaimer, the term of this patent is extended or adjusted under 35 U.S.C. 154(b) by 10 days.

(21) Appl. No.: 09/742,834

(22) Filed: Dec. 20, 2000

(65) Prior Publication Data

US 2002/0077575 A1 Jun. 20, 2002

(51) Int. Cl.[7] .................................................. A61F 5/00
(52) U.S. Cl. ...................................... 602/26; 128/116.1
(58) Field of Search .................. 602/5–8, 19; 128/96.1, 128/112.1, 115.1, 116.1; 2/44, 45, 92

(56) References Cited

U.S. PATENT DOCUMENTS

| | | | |
|---|---|---|---|
| 5,232,424 A | * | 8/1993 | Pearson et al. ............. 482/106 |
| 5,295,951 A | * | 3/1994 | Fareed ........................ 602/62 |
| 5,433,697 A | | 7/1995 | Cox |
| 5,501,697 A | * | 3/1996 | Fisher |
| 5,512,056 A | * | 4/1996 | Stevens et al. |
| 5,672,150 A | | 9/1997 | Cox |
| 5,695,520 A | * | 12/1997 | Bruckner et al. |
| 6,007,508 A | * | 12/1999 | Reinhardt et al. ............ 602/62 |

* cited by examiner

*Primary Examiner*—Nicholas D. Lucchesi
*Assistant Examiner*—Lalita M. Hamilton
(74) *Attorney, Agent, or Firm*—Malin, Haley & DiMaggio, P.A.

(57) ABSTRACT

A brace for the knee area of the user, which includes a front component and a back component further including one or more protrusions, which may be hemispherical in shape, that protrude from the inner surface of the back component such that the one or more protrusions acts upon the back of the leg when the back component is releasably attached to and firmly on the leg and a fastener for connecting the front component and the back component.

2 Claims, 3 Drawing Sheets

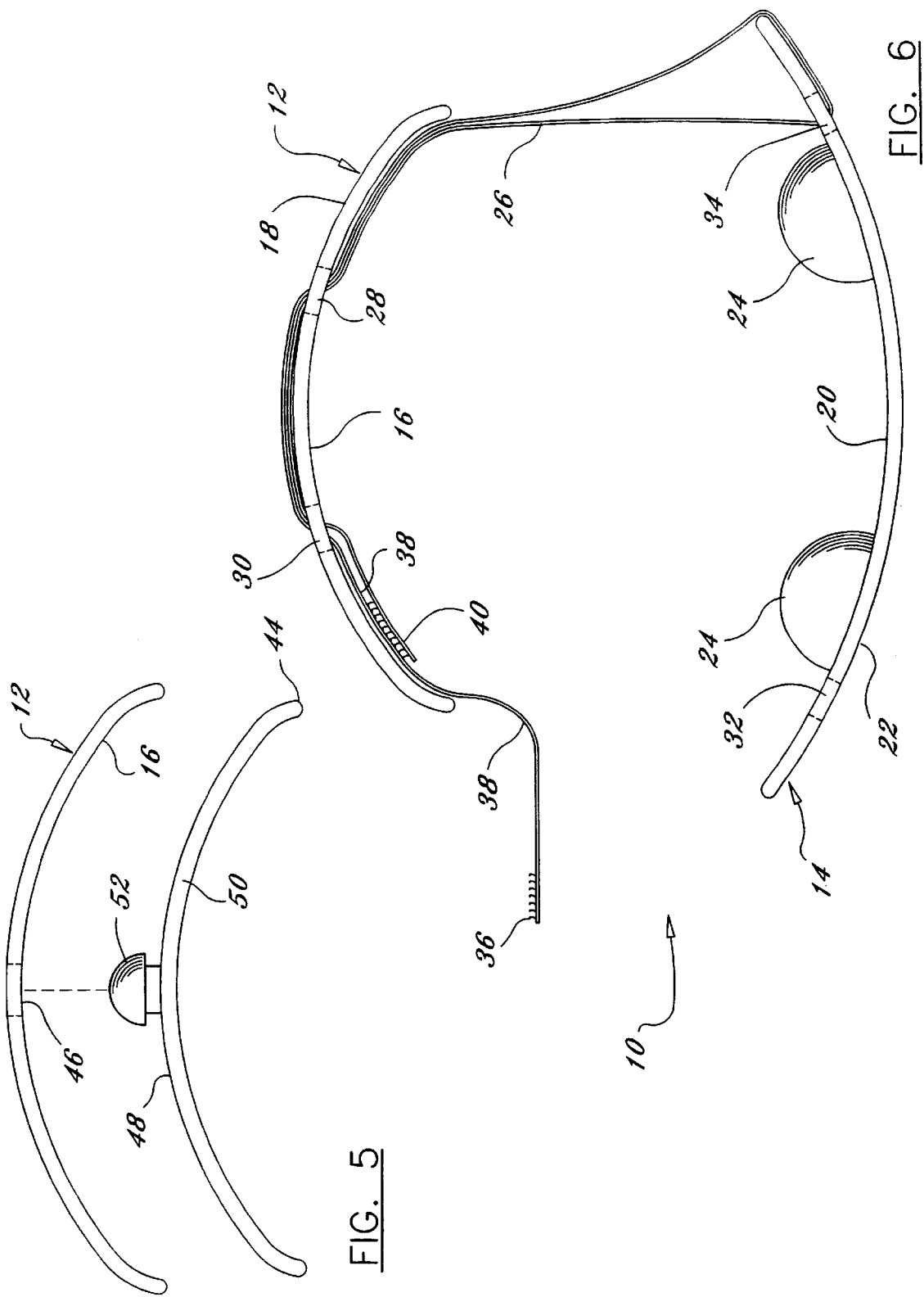

KNEE BRACE

BACKGROUND OF THE INVENTION

1. Field of the Invention

The present invention relates primarily to a leg brace for the healing of and the relief from pain from leg muscle and cartilage ailments and conditions in the area surrounding the knee, wherein protrusions depress into the muscle areas behind and below the knee thereby increasing blood circulation in the areas of the protrusions.

2. Description of Related Art

As years go by, people pile up miles of activity and tons of stress on their knees. Over a person's lifetime, several types of injuries and diseases affecting the knee and surrounding area may occur. For example, tendonitis, patellar tendonitis, chondromalacia disease, Osgood Schlatter's disease, chondromalacia patella syndrome and osteoarthritis all may limit a person's mobility, adversely affecting that person's quality of life. A person may also have irritation, inflammation and cartilage wear around and under the patella which could otherwise be prevented. Furthermore, pain may be aggravated by trauma to the knee.

In order to alleviate pain in the knee or prevent pain from occurring, it is necessary to utilize a device that can provide support in the knee area and simultaneously stimulate beneficial blood flow. A form of opposing force bracing is the best method possible, while protrusions that press firmly into the back of the leg stimulate blood flow in the leg. In addition, the location of these protrusions may coincide with points on the leg where acupuncture would be performed.

Recent research has shown that the use of protrusions with a brace provides effective relief from pain. Applicant's U.S. Pat. No. 5,433,697 ("'697") used a series of protrusions which come into contact with the back muscles. Although the '697 device worked well for back pain, the present invention is a substantial improvement in knee and leg bracing devices. Applicant's U.S. Pat. No. 5,672,150 for a wrist brace/palm support immobilizes a wrist, but does not provide stimulation to the wrist area at all.

Thus, it is apparent that it was necessary to provide a device which would provide support in the knee area and simultaneously stimulate beneficial blood flow in the leg. The protrusions of the present device ensure better compression and support and enables quicker healing through use of the device. The device may be worn while sedentary or during strenuous physical activity.

BRIEF SUMMARY OF THE INVENTION

The present invention is a brace for the knee area, comprising a front component, a back component with one or more protrusions from the inner surface of the back component such that the one or more protrusions presses against the back of a leg when the back component is releasably attached to and firmly on the leg and a fastener for connecting the front component and the back component which provides an opposing clamping force upon the front component to the front of the leg and upon the back component to the back of the leg. In another embodiment, the front component is generally concave. In yet another embodiment, the front component has a dip in its top to accommodate movement of a person's patella and the front component extends to protect the lower tendons of the patella. In yet another embodiment, ventilation holes are formed through the front component and the back component. In still another embodiment, the back component comprises crisscross construction between the protrusions. In yet still another embodiment, the protrusions are horizontal orientation in the central portion of the interior surface of the back component.

In another embodiment, the protrusions are hemispherical and ½ inch deep and 1 inch in diameter. In yet another embodiment, the protrusions are concave, thereby providing concave depressions inward from the outer surface of the back component. In yet still another embodiment, the protrusions are positioned such that they press firmly against the muscles of the back of the leg in areas where acupuncture would be performed on the leg.

In another embodiment, the fastener for connecting the front component and the back component comprises a strap comprising a hook and loop fastener material. In still another embodiment, the front component further comprises a vertical slot on the left side and a vertical slot on the right side, and the back component also has a vertical slot on the left side and a vertical slot on the right side. In yet another embodiment, the fastener comprises at least one strap comprising hook and loop fastener material that is disposed through the left slot and the right slot on the front component and through the left slot and right slot of the back component. In still another embodiment, the fastener comprises two straps.

In yet still another embodiment, the front component further comprises a pad on the inside surface of the front component, attached by a hole formed through the front component and a member protruding from an outer surface of the pad which fits through the hole. In still another embodiment, an adhesive attaches the pad. In yet another embodiment, the fastener for the front component and the back component is a generally elastic fabric loop attached to the outer surface of the front component and the outer surface of the back component.

In accordance with these and other objects which will become apparent hereinafter, the instant invention will now be described with particular reference to the accompanying drawings.

BRIEF DESCRIPTION OF THE DRAWINGS

FIG. 5 illustrates a side view of the pad and back component of one embodiment.

FIG. 6 illustrates a top view of one embodiment.

In accordance with these and other objects which will become apparent hereinafter, the instant invention will now be described with particular reference to the accompanying drawings.

DESCRIPTION OF THE PREFERRED EMBODIMENT

With reference to FIGS. 1–6, the brace is shown generally at 10. The brace has a front component 12 and a back component 14. The front component 12 and the back component 14 may be formed of rubber, thermoplastic, composites, metal or other appropriate materials known in the art. Furthermore, the front component 12 and the back component 14 may be made from transparent, translucent or opaque material. The front component 12 and the back component 14 are generally rigid. However, there may be some flexibility depending upon the materials used and the manufacturing method.

Figure 3:
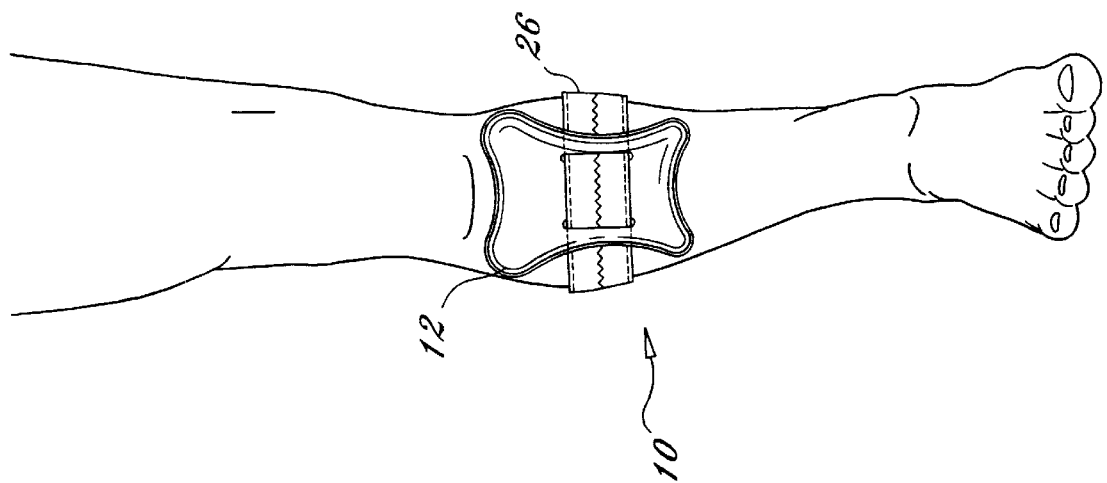
FIG. 3 illustrates a front view of one embodiment in use.
Figure 2:
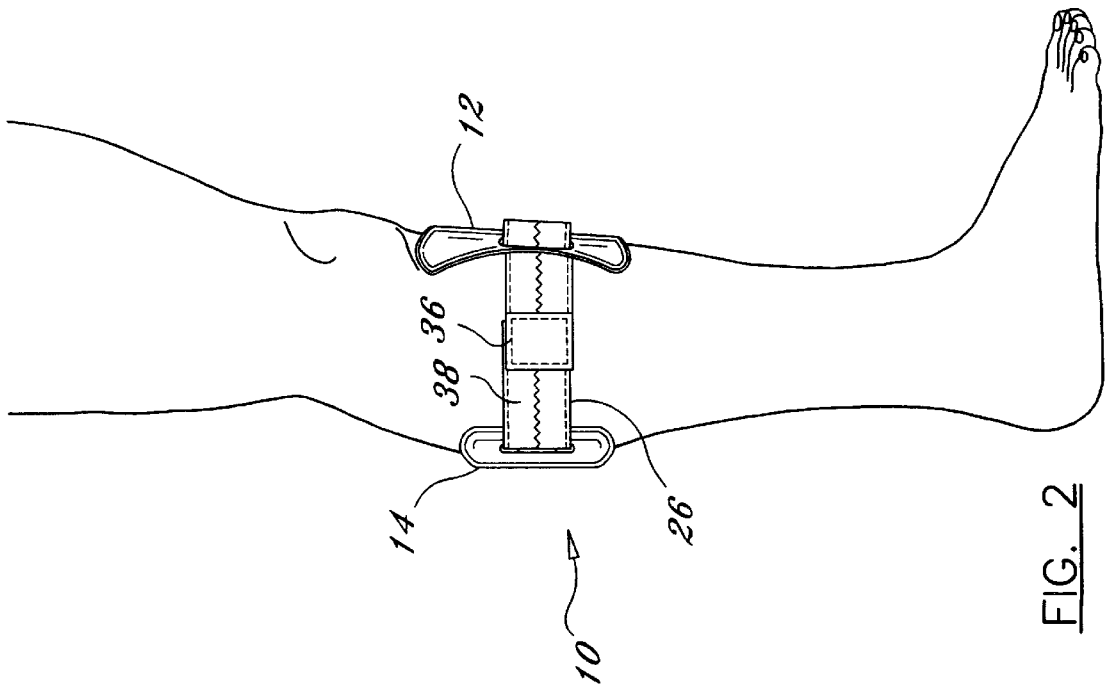
FIG. 2 illustrates a side view of one embodiment in use.

The front component 12 comprises an inner surface 16 and an outer surface 18. Furthermore, the front component 12 is generally concave in shape so that it forms a plate over the patella region of the leg when in use, as shown in FIGS. 2 & 3. In one embodiment, the front component 12 has a dip at the top portion to accommodate movement of the patella. The front component 12 may also extend to protect the lower tendons of the patella. The front component 12 is approximately 3" wide by 4.5" long; however, the front portion can be larger or smaller to fit larger or smaller people. In addition, the front component 12 may have one or more ventilation holes (not shown) drilled through it.

The back component 14 is generally concave in shape to fit over the back portion of a person's lower leg. The back portion may be contoured to provide comfort to the user. The back component 14 also comprises an inner surface 20 and an outer surface 22. The inner surface 20 of the back component 14 further comprises one or more protrusions 24 extending outward from the inner surface 20 of the back component 14. In a preferred embodiment, the protrusions 24 are hemispherical in shape. However, other shapes for the protrusions 24 are also contemplated. In addition, the protrusions 24 themselves may be concave. Thus, the protrusions 24 outward from the inner surface 20 also form concave depressions inward from the outer surface 22. In addition, ventilation holes (not shown) may be drilled through the back component 14. Also, the back component 14 may have an open criss-cross or weave construction between the protrusions 24 to aid in ventilation.

Figure 1:
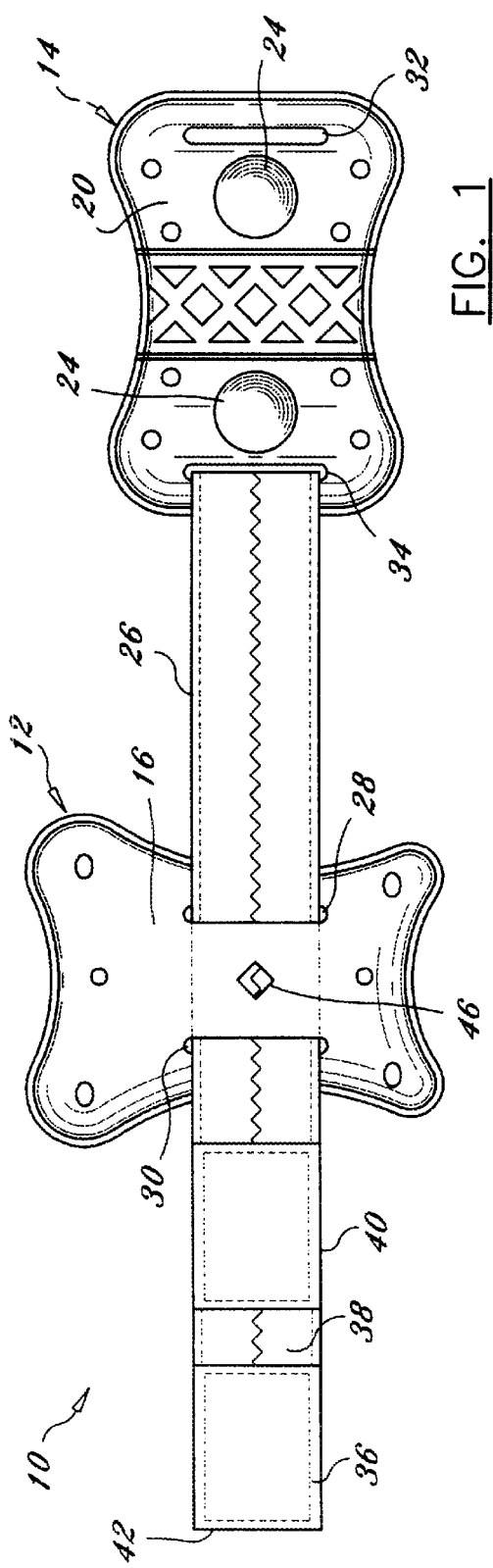
FIG. 1 illustrates a front view of the interior of one embodiment.
Figure 4:
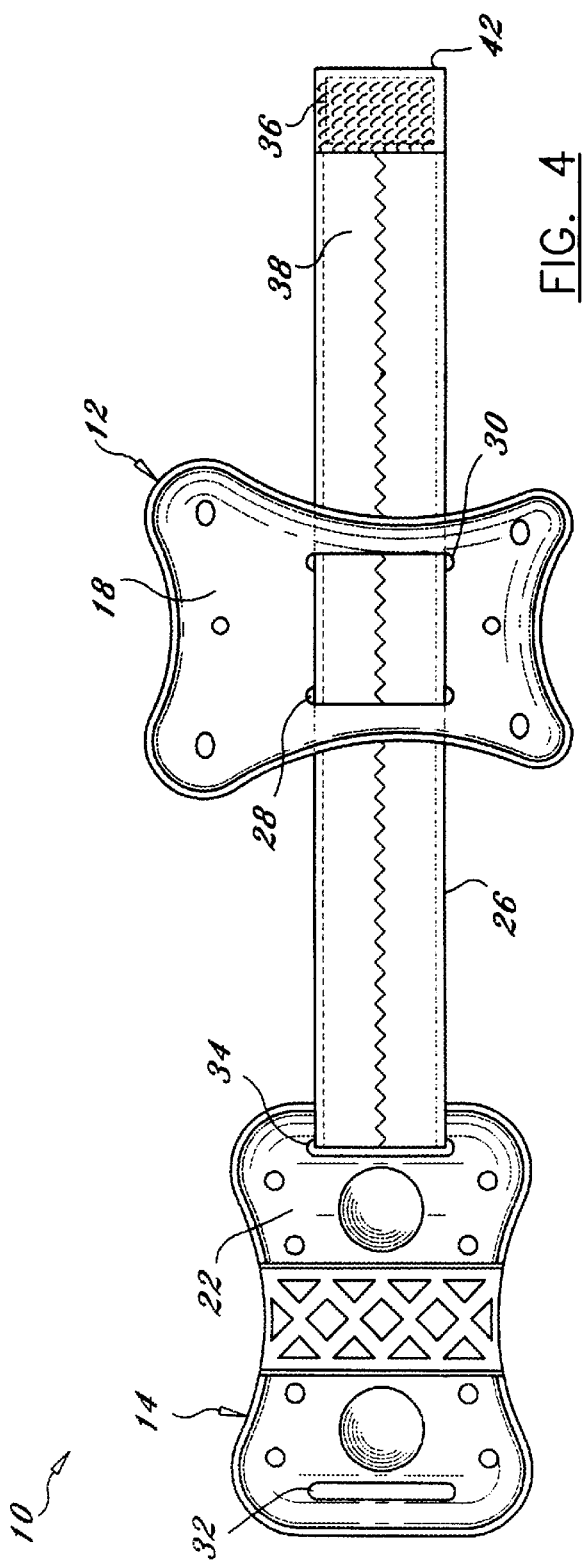
FIG. 4 illustrates a front view of the interior of one embodiment.

As shown in FIGS. 1, 4 and 6, two protrusions 24 may be in horizontal orientation on the inner surface 20 of the back portion 12, and separated by a predetermined distance. The protrusions 24 are positioned such that they press firmly against the muscles of the back of the leg in areas where acupuncture would be performed when the brace 10 is attached to a person's leg. The one or more protrusions 24 may be hemispheric domes in shape, and approximately ½ inch in depth and one inch in diameter. The protrusions themselves may be made from transparent or translucent material. As shown, the two protrusions 24 apply mild pressure to the Gastrocnemius muscle as well as the Peroneus Longus muscle.

The front component 12 and the back component 14 are connected by a fastener for connecting the front component 12 and the back component 14 which provides an opposing clamping force upon the front component 12 to the front of the leg and upon the back component 14 to the back of the leg. One example of such fastener for connecting is a strap 26 as shown in FIGS. 1 through 4 and 6. At least one set of vertical slots 28, 30 are made through the left side and the right side of the front component 12. At least one set of vertical slots 32, 34 are also made through the left side and the right side of the back component 14. As also shown in FIGS. 1 through 4 and 6, a strap 26 may be passed through the slots 28, 30 located near the sides of the front component 12 and through the slots 32, 34 located near the sides of the back component 14.

Thus, when the brace 10 is in use, the fastener for connecting the front portion 12 and the back portion 14, such as the strap 26, keeps the front portion 12 and the back portion 14 releasably attached to and firmly in place on the person's leg. In addition, the front component 12 and the back component 14 and the fastener supply support to the Peroneus Longus and Soleus muscles.

The fastener for connecting provides an opposing clamping force on both the front portion 12 and the back portion 14, applying compressive force between the protrusions 24 on the inner surface 20 of the back portion 14 and the person's lower leg at the points where acupuncture would be performed. Isometric toning of the muscle area surrounded by the device 10 is constant through the application of opposing force bracing. The protrusions 24 assist in the healing of Tendonitis caused by irritation of a rope-like muscle that is directly attached to the bone of the leg. The device 10 assists in the healing of inflamed tendons and adds preventive maintenance and protection while the wearer is active.

The strap 26 may be of hook and loop material, so that the strap 26 may be secured by attaching a hook portion 36 of the strap 26 with a loop portion 38 of the strap 26. The strap 26 may form a loop by attaching the hook portion 36 at a first end 40 of the strap to the loop portion 38 of the strap 26. The strap 26 forms the loop after being disposed through a left slots 30 and a right slot 28 in the front component 12 and a right slot 34 in the back component 14, as shown in FIG. 6.

As shown in FIGS. 2 and 3, once the brace 10 is in place around the leg, the second end 42 of the strap 26 is disposed through a left slot 32 in the back component 14 and cinched tightly. The invention as used is illustrated in FIGS. 2 and 3.

Furthermore, other methods of disposing a strap 26 of hook and loop fastener through the front component 12 and the back component 14 are also contemplated. Also, other methods of connecting the front component 12 and the back component 14 which provide an opposing clamping force upon the front component 12 to the front of the leg and upon the back component 14 to the back of the leg, keeping the brace 10 in place and tight against the leg are known in the art and are contemplated herein.

In another embodiment, a fastener for attaching a pad 44 to the inside surface 16 of the front component 12 is contemplated. Illustrated in FIGS. 1–5, a hole 46 is formed through the central portion of the front component 12. The hole 46 may be formed at the time of manufacture of the front component 12 or afterward. In one embodiment, a pad 44 with an outer surface 48 and an inner surface 50 is attached to the front component 12 with a member 52 protruding from the outer surface 48 of the pad 44 that fits through the hole 46 and releasably attaches the pad 44 to the inner portion 16 of the front component 12. In yet another embodiment, the pad 44 is attached to the inner surface 16 of the front component 12 by an adhesive. Other fasteners for attaching the outer surface 48 of the pad 44 to the inner surface 16 of the front component 12, either mechanically or chemically, are also contemplated. In addition, the pad 44 may be permanently or releasably attached to the inner portion 16 of the front component 12. Thus, the pad 44, when affixed, improves the efficiency of the quadriceps muscle and protects the knee from anterior impact. When the patella does not track properly in the femoral groove, a person can develop patellofemoral malalignment which elicits pain when the knee is bent or straightened. The pad 44 helps the patella relocate to the proper position in the femoral groove. Thus, the pad 44 provides excellent traction and comfort.

Alternatively, the fastener for connecting the front component 12 and the back component 14 which provide an opposing clamping force upon the front component 12 to the front of the leg and upon the back component 14 to the back of the leg may be two straps: one strap passing through right slot 30 of the front plate 12 with the left slot 32 of the back component 14 and a second strap passing through the left slot 28 of the front component 12 with the right slot 34 of the back component 14. In this embodiment, either or both of the two straps may be made of hook and loop material so that one or both sides may be cinched tightly. Other strap materials known in the art are also contemplated.

As another alternative, a generally elastic fabric loop is attached to the outer surface 18 of the front component 12 and the outer surface 22 of the back component 14. The attachment may be by glue, epoxy or other adhesive, or by mechanical or other means known in the art. The attachment keeps the front component and the back component in proper alignment on the leg and keeps the components 12, 14 firmly against the leg.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A brace for the knee area, comprising;

a front component;

a back component, further including one or more protrusions from the inner surface of the back component such that the one or more protrusions presses against the back of a leg when the back component is releasably attached to and firmly on the leg; and a fastener for connecting the front component and the back component which provides an opposing clamping force upon the front component to the front of the leg and upon the back component to the back of the leg;

wherein the back component comprises criss-cross construction between the one or more protrusions.

2. A brace for the knee area, comprising:

a front component;

a back component, further including one or more protrusions from the inner surface of the back component such that the one or more protrusions presses against the back of a leg when the back component is releasably attached to and firmly on the leg; and a fastener for connecting the front component and the back component which provides an opposing clamping force upon the front component to the front of the leg and upon the back component to the back of the leg;

wherein the front component further comprises;

a fastener for attaching a pad to the inside surface of the front component: and a pad;

wherein the fastener for attaching a pad to the inside surface of the front component comprises a hole formed through the front component, and a member protruding from an outer surface of the pad which fits through the hole through the front component.

* * * * *